United States Patent [19]
Takahashi

[11] Patent Number: 5,773,004
[45] Date of Patent: Jun. 30, 1998

[54] COMPOSITIONS FOR CURING DIABETES MELLITUS, PROCESSES FOR THE PREPARATION OF SAME, AND USAGE OF SAME

[76] Inventor: Masakiyo Takahashi, 12-15, Minamikatae 5-chome, Johnan-ku, Fukuoka 814-01, Japan

[21] Appl. No.: 550,078

[22] Filed: Oct. 30, 1995

[30] Foreign Application Priority Data

Oct. 31, 1994 [JP] Japan ..................................... 6-267860

[51] Int. Cl.$^6$ ............................. A01N 65/00; A23F 3/34; A61K 45/00; A61K 35/78
[52] U.S. Cl. ...................... 424/195.1; 426/425; 426/435; 426/590; 426/597; 426/655; 514/783; 514/866; 514/884
[58] Field of Search ................................. 424/195.1, 127; 426/597, 425, 435, 590, 655; 514/25, 884, 783, 866

[56] References Cited

U.S. PATENT DOCUMENTS 4,544,550  10/1985  Rodolfo .................................. 424/127

FOREIGN PATENT DOCUMENTS 1081825   2/1994   China ............................. A23F 3/14
02264722  10/1990  Japan ........................... A61K 31/365

OTHER PUBLICATIONS

Lin et al. 1993 Phytotherapy Research vol. 7 pp. 305–309, Jul. 1993.
Takahashi et al 1985 Planta Medica 2 pp. 100–101, Apr. 1, 1985.
Shin et al. 1993 Fitoterapia 64 (2) 130–135, Feb. 1, 1993.
Foster et al. 1990 A Field Guide to Medicinal Plants Houghton–Mifflin, Boston, Jan. 1, 1990.
Goldberg et al. 1994 Alternative Medicine Future Medicine Publishing WA. pp 647–655, Jan. 1, 1994.
Nakashima et al. 1993 j Natural Products 56 (3) 345–350, Mar. 1, 1993.
Kako et al. 1995 Biol Pharm Bull 18 (5) 785–787, May 1, 1995.
Yoshikawa et al. Chem Pharm Bull 43 (11) 1878–1882, Nov. 1, 1995.

*Primary Examiner*—Michael P. Woodward
*Assistant Examiner*—Mary K. Zeman
*Attorney, Agent, or Firm*—Foley & Lardner

[57] ABSTRACT

Disclosed is the composition for treating or curing diabetes mellitus containing an ingredient or component suitable for treatment of diabetes mellitus from an extract obtained by immersing a plant belonging to genus Tithonia and/or Ludwigia in a pharmacologically acceptable solvent for a pre-determined period of time, said plant belonging to genus Tithonia being *Tithonia diversifolia* (Hemsl.) A. Gray, *Tithonia rotundifolia* (Mill) Blake, *Tithonia fruticosa* Canby & Rose, *Tithonia scaberrima* Benth. or *Tithonia longeradiata* (Bertol) Brake; and said plant belonging to genus Ludwigia being *Ludwigia octovalvis* Raven or *Ludwigia prostrata* Roxb. or *Ludwigia epilobioides* Maxim. The composition administered in the form of tea or drink or other formulation to a diabetic patient by first applying a composition containing an extract from the plant belonging to genus Tithonia and thereafter applying a composition containing an extract from the plant belonging to genus Ludwigia. The composition for treating diabetes mellitus can alleviate or diminish a variety of symptoms caused by diabetes mellitus or prevailing among diabetic patients, thereby naturally reducing or lowering blood glucose levels to a normal range and preventing diabetes mellitus to be caused to reoccur for a long period of time without continuously administering the composition.

8 Claims, 3 Drawing Sheets

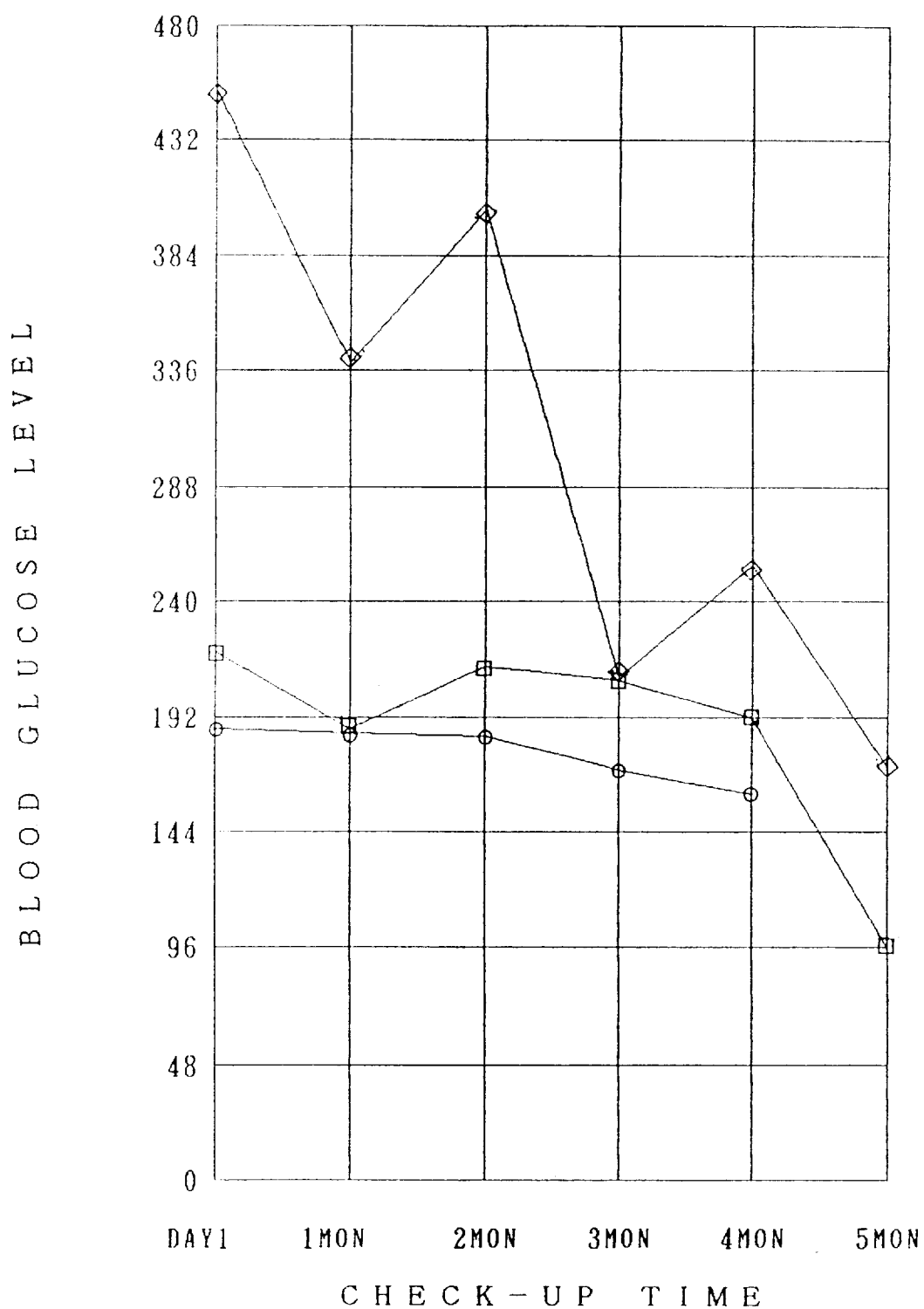

COMPOSITIONS FOR CURING DIABETES MELLITUS, PROCESSES FOR THE PREPARATION OF SAME, AND USAGE OF SAME

BACKGROUND OF THE INVENTION

1. Field of the Invention

The present invention relates to a composition for curing or treating diabetes mellitus, a process for the preparation of the same, and usage of the same and, more particularly, to a composition for curing or treating diabetes mellitus, a process for the preparation of the same, and usage of the same, the composition having as a major component an extract containing a protein polysaccharide obtained from a certain kind of plant and being capable of lowering or reducing a level of glucose in the blood of a patient suffering from diabetes mellitus by alleviating or ameliorating various symptoms caused by or associated with the diabetes mellitus as well as preventing the glucose level in the blood of the diabetic patient with high certainty from arising again.

2. Description of the Related Art

Diabetes mellitus is the disease that may cause a variety of symptoms due to a rise in a level of glucose in the blood (blood glucose level) on account of the insufficient action of insulin secreted from β-cells of the Langerhans' islands of the spleen. A committee of the WHO indicates the classification of the diabetes mellitus as insulin-dependent diabetes mellitus (IDDM), non insulin-dependent diabetes mellitus (NIDDM), malnutrition (diabetes mellitus (MRDM)) and so on. Among patients with diabetes mellitus, approximately 90% of the diabetes mellitus are of the non-insulin-dependent diabetes mellitus (NIDDM) type. In addition, patients with impairment of glucose tolerance (IGT) and gravidic diabetes mellitus (GDM) are classified as patients having the risk that their diseases may advance or develop to diabetes mellitus.

Further, as is well aware, the diabetes mellitus is a risk factor causing arteriosclerotic disorders that in many cases may involve in a cause of a great number of disorders and, in worse cases, death.

For healthy persons, the glucose level in the blood (blood glucose level) is maintained at the level ranging normally from 70 mg to 140 mg per dl due to the action of a variety of hormones including insulin, glucagon and so on. The blood glucose level indicates the figure representing an extent of conditions or symptoms caused by or associated with diabetes mellitus. If the blood glucose level would be outside the normal range, i.e. lower than the lowest level of the normal range or higher than the uppermost level thereof, the life may be endangered. Particularly, if the blood glucose level would be a half of the normal level, on the one hand, such a low blood glucose level is life threatening. If the blood glucose level would be too high, on the other hand, it may cause a variety of symptoms hazardous to the human health, including diabetes mellitus. In order to maintain the blood glucose level within the normal range, diabetes mellitus is frequently treated using a combination of diet therapy with ergotherapy, insulin therapy, pharmaceutical therapy and so on.

For the insulin therapy, there has extensively been applied pork insulin and, particularly in recent years, human insulin produced through genetic engineering, which is intravenously administered. For the pharmaceutical therapy, there have been applied various pharmaceuticals including orally administrable drugs, for example, of sulfonyl urea type, sulfonamide type, and biguanide type. These drugs can lower or reduce the blood glucose level of patients suffering from diabetes mellitus, thereby relaxing or eliminating the various symptoms caused by or associated with diabetes mellitus. However, there has so far been developed yet any effective pharmaceutical that can alleviate or relax the symptoms of diabetes mellitus, thereby capable of lowering or reducing the blood glucose level of patients suffering from diabetes mellitus.

Further, an immunosuppressive agent referred to as cyclosporin A can relax the symptoms of diabetes mellitus when it is administered to a patient having insulin-dependent diabetes mellitus of an initial stage. This agent has the problem, however, which may cause side effects.

SUMMARY OF INVENTION

As a result of extensive research and studies of extracts from a variety of plants, it has been found that an extract of a particular plant contains a protein polysaccharide that can lower or reduce the blood glucose level of patients suffering from diabetes mellitus, thereby alleviating or eliminating or relaxing various symptoms or states of diabetes mellitus as well as preventing the blood glucose level from arising again for a prolonged period of time and, as a consequence, being useful for curing or treating diabetes mellitus. The present invention has been completed on the basis of this finding.

Therefore, the present invention has an object to provide a composition for treating or curing diabetes mellitus, which comprises an extract containing a protein polysaccharide obtained from a particular plant as a major ingredient or component and which can lower or reduce the blood glucose level of a patient suffering from diabetes mellitus by alleviating or relaxing various symptoms or conditions of the diabetes mellitus as well as being capable of preventing the blood glucose level thereof from arising again for a prolonged period of time.

The present invention has another object to provide a method for the preparation of the composition for treating or curing diabetes mellitus according to the present invention.

Further, the present invention has an object to provide a use of the composition according to the present invention for treating or curing diabetes mellitus.

In order to achieve the objects of the present invention, it provides a composition for treating or curing diabetes mellitus useful and suitable for the treatment or curing of the diabetes mellitus, which has as a major ingredient or component an extract containing a protein polysaccharide obtained from a particular plant, more specifically, a plant belonging to the genus Tithonia or genus Ludwigia.

In a particularly preferred aspect of the present invention, the present invention provides the usage of the composition for curing or treating diabetes mellitus, in which a composition containing an extract of the plant belonging to genus Tithonia to which an extract of another plant or the like may be added as a secondary ingredient or component is first administered for a certain period of time and a composition containing an extract of the plant belonging to genus Ludwigia to which an extract of another plant or the like may be added as a secondary ingredient or component is then administered for a certain period of time, preferably shorter than the period of time during which the former is administered.

The other objects, features and advantages of the present invention will become apparent in the course of the description which follows with reference to the accompanying drawings.

*sifolia* (Hemsl.) A. Gray, is first administered and the extract of plant species *Ludwigia octovalvis* Raven is then administered.

Figure 1:
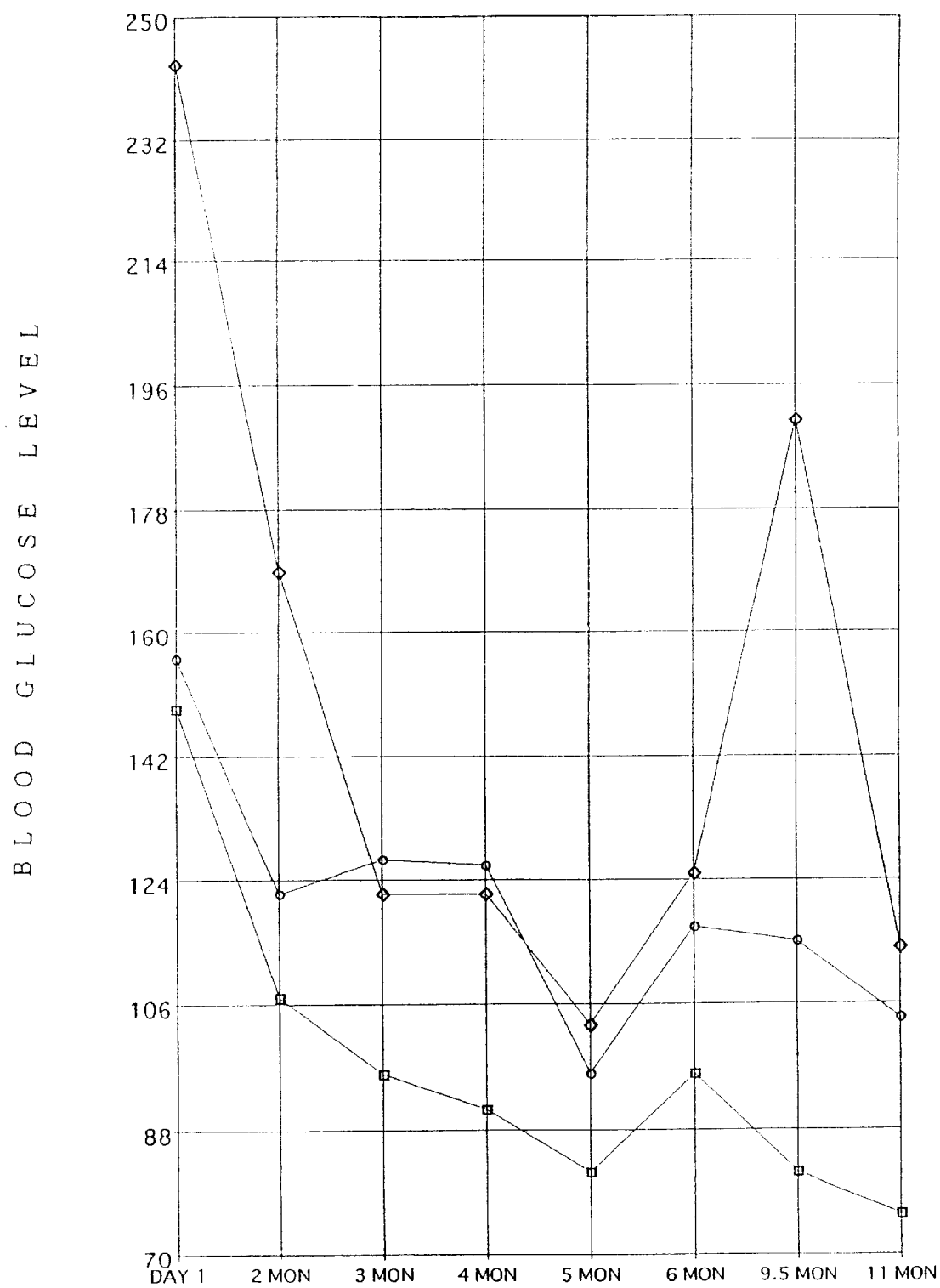
FIG. 1 is a graph showing the test results for Case No. 2 below, in which the extract of plant species, *Tithonia diver-*
Figure 2:
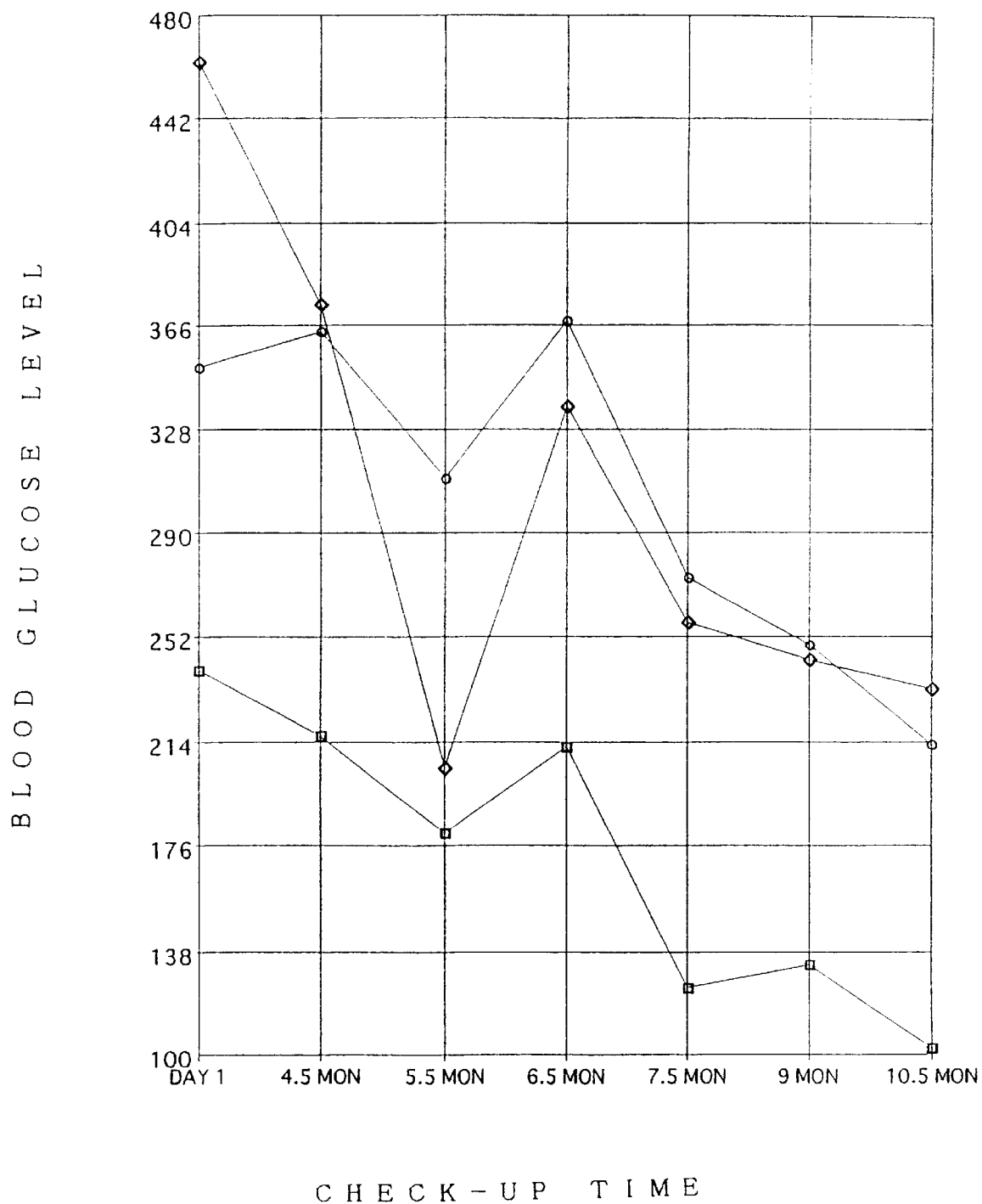

FIG. 2 is a graph showing the test results for Case No. 3 below, in which the extract of plant species, *Tithonia diversifolia* (Hemsl.) A. Gray, is first administered and the extract of plant species *Ludwigia octovalvis* Raven is then administered in substantially the same manner as in FIG. 1.

FIG. 3 is a graph showing the test results for Case No. 4 below, in which the extract of plant species, *Tithonia diversifolia* (Hemsl.) A. Gray, is first administered and the extract of plant species *Ludwigia octovalvis* Raven is then administered in substantially the same manner as in FIG. 1.

DESCRIPTION OF THE PREFERRED EMBODIMENTS

As described hereinabove, the composition for curing or treating diabetes mellitus according to the present invention comprises an extract obtained from a plant belonging to genus Tithonia or Ludwigia as a primary ingredient or component, which may contain an extract obtained from a different kind of plant, a vitamin, chitin or chitosan as a secondary ingredient or component The plants belonging to the genus Tithonia of the family Compositae may include plant species such as, for example, *Tithonia diversifolia* (Hemsl.) A. Gray; *Tithonia fruticosa* Canby & Rose; *Tithonia scaberrima* Benth.; *Tithonia longeradiata* (Bertol) Blake; and *Tithonia rotundifolia* (Mill) Blake.

More specifically, *Tithonia diversifolia* (Hemsl.) A. Gray is originated from China, Mexico, and Central African countries and contains a small amount of pyrethrin. Leaves of the plant species *Tithonia scaberrima* Benth. have been utilized for a cure of fever and rigor in El Salvador.

As the plants belonging to the genus Ludwigia of the family onagaraceae, on the other hand, there may be mentioned, for example, *Ludwigia octovalvis* Raven, *Ludwigia prostrate* Roxb. and *Ludwigia epilobioides* Maxim.

In the description of this specification which precedes and follows, the term "plant" referred to therein is intended to mean a plant belonging to the genus Tithonia and/or Ludwigia, which can be employed for the present invention, unless otherwise stated.

The composition for treating or curing diabetes mellitus according to the present invention may contain a secondary ingredient or component, as desired, in addition to the major ingredient or component extracted from the plant belonging to the genus Tithonia or Ludwigia.

As the secondary ingredient or component that may be added to the primary ingredient or component as described hereinabove as needed, there may be mentioned, for example, an extract containing an ingredient or component extracted from another plant, a vitamin, chitin or chitosan.

A description will be made of such another plants whose ingredients and/or components may be added to the primary ingredient or component contained in the extract extracted from the plant belonging to the genus Tithonia or Ludwigia. Such another plants may include, for example, Aralia elata Seemann; *Rerhmannia glutinosa* Libosch. var. purpurea Makino; *Panax ginseng* C. A. Mayer; *Trichosanthes kirilowii* Maxim; *Glycyrrhiza glabra* L. var. *glandulifera* Regel et Herder; *Glycyrrhiza uralensis* Fischer; *Ophiopogonis tuber*; *Anemarrhena asphodeloides* Runge; *Poria cocos* Wolf; *Pueraria lobata* Ohwi or *Pueraria pseudohirsuta* Tanget Wang.; *Schizandra chinensis* (Turcz) Baill; *Glechoma hederacea* L. var. *grandis* (A. Gray) Kudo; *Portulaca oleracea* L.; *Taraxacum japonicum* Koidz.; *Lycium chinense* Mill.; *Pueraria lobata* (Willd.) Ohwi; *Smilax china* L.; and *Lepisorus thunbergianm* (Kaulf.) Ching.

More specifically, Aralia elata Seemann is utilized in the form of a liquid as tea or drink. The liquid in the amount of a daily dosage can be produced, for example, by immersing 20 grams of the dry coats of its bark or its dry roots in 1,000 ml of a hot water.

*Rerhmannia glutinosa* Libosch. var. *purpurea* Makino is known as containing eight kinds of polysaccharides such as, for example, catalpol glycoside, iridoid glycoside and stachyose, mannitol, amino acids such as, for example, arginine, phosphoric acid and so on. It may be utilized in the form of an extract, or *Rerhmanniae radix*, obtained, for example, by placing its dry roots in a hot water. The extract may be applied in a daily dosage of five grams. This extract can supplement to the major ingredient or component for the treatment of diabetes mellitus because of its action as a supplement to the blood, an antasthenic or a hemostatic.

*Panax ginseng* C.A. Mayer contains ingredient or components that can add its own action as an antasthenic to the effects of treating or curing diabetes mellitus performed by the primary ingredient or component, thereby supplementing the actions of the primary ingredient or component by treating or curing the disorders of the metabolism of saccharides and a decrease in the other metabolism. Such disorders of the mechanism prevail among patients with diabetes mellitus and complications therewith and accelerating the hemokinesis and urination of patients therewith. A daily dosage of the extract from the plant species *Panax ginseng* may preferably may be approximately three grams.

*Trichosanthes kirilowii* Maxim contains a large amount of proteins having the amino acid component as represented by $H_2NCONH-(CH_2)3CH(NH_2)COOH$. The addition of an extract from this plant species can exhibit the action of terminating a thirst from which patients with diabetes mellitus are suffering to a severe extent, thereby supplementing the actions of the primary ingredient or component of the composition for treating or curing diabetes mellitus according to the present invention.

*Glycyrrhiza glabra* L. var. *glandulifera* Regel et Herder or *Glycyrrhiza uralensis* Fischer contains glycyrrhizin that is used as an excipient or a sweetener for formulating various preparations, particularly tablets, for medicinal use. A daily dosage of an extract from this plant may preferably be approximately five grams.

*Ophiopogonis tuber* may be used by immersing a dry root tuber of a plant belonging to the genus Ophiopogonis. An ingredient contained in the extract therefrom has the action of treating or curing inflammation, thereby capable of treating or curing an inflammation caused by suppuration which it is difficult to treat or cure particularly for patients with diabetes mellitus. The extract from this plant species may provide the diabetic patients with an antasthenic action. A recommendable daily dosage preferably may be approximately four grams.

*Anemarrhena asphodeloides* Runge contains a variety of steroid sapogenins, e.g. sarsasapogenin and markogenin, and sacchardies, e.g. saponin and mangiferin as a xanthone saccharide derivative. An addition of an extract from this plant to the major ingredient or component can serve for the alleviation of fever, urination, refreshment, tranquility and so on. The extract therefrom can provide a supplement to the treatment of diabetes mellitus by the major ingredient or component. A recommended daily dosage preferably may be approximately four grams as the weight of the extract.

*Poria cocos* Wolf may be used in the form of a sclerotium with its outer skin removed therefrom and it contains a variety of polysaccharides and tetracyclic triterpenes. An extract of the sclerotia of the plant species Poria cocos Wolf has the action of urination and tranquility and is effective for treating disorders of the eyes of diabetic patients, particularly such as turnsick or vertigo or diplopia. Further, it can treat the convulsion of the calf which often attacks diabetic patients because it is useful for the treatment or prevention of the clonic convulsion of the muscle. A recommended daily dosage preferably may be approximately six grams as the weight of extract.

*Pueraria lobata* Ohwi or *Pueraria pseudohirsuta* Tanget Wang contains starch and isoflavone derivatives and has the action for the sweating, alleviation of fever and relaxation. It is effective particularly for the relaxation of the nuchal muscle of a diabetic patient and also useful for the treatment of the neurotic disorders thereof. A recommended daily dosage preferably may be approximately eight grams as the weight of extract.

*Schizandra chinensis* (Turcz) Baill contains schizandrin, gomisin, sesquiterpenes and organic acids such as citric acid, malic acid, tartaric acid and so on. An extract of this plant is effective for the treatment of a severe feeling of fatigue or malaise, which attacks a majority of patients with diabetes mellitus, and for the prevention of a stress ulcer of the stomach. Further, it is effective for the treatment of disorders of the liver. A recommended daily dosage preferably may be approximately three grams as the weight of extract.

*Glechoma hederacea L. var. grandis* (A. Gray) Kudo can treat an early stage of some diseases of the kidney and impotence so that its addition to the primary ingredient or component may be effective for the treatment of juvenile diabetic patients. It is also useful for the treatment of cure of chronic infectious diseases of the urinary tract, such as cystitis, urethritis and so on. In addition, it is useful for the treatment or cure of neurotic disorders caused by or associated with diabetes mellitus. A recommended daily dosage may be taken in the form of a liquid as tea or drink produced, for example, by immersing fifteen grams of entire portions of the dried plant in an appropriate volume of water.

*Portulaca oleracea* L. is effective for treating disorders of the functions of the liver from which a great number of diabetic patients are suffering so that its addition to the primary ingredient or component may be useful for the treatment of the disorders of the liver functions. It is particularly difficult to treat or cure an ulcer caused by diabetes mellitus so that the addition thereto can make it easy to cure such an ulcer. Further, it is effective for the treatment of fatigue or malaise. This addition, however, is inappropriate for pregnant patients or diabetic patients with hypersensitive enteritis. A recommended daily dosage may be taken in the form of a liquid as tea or drink produced, for example, by immersing five to ten grams of entire portions of the dried plant in an appropriate volume of water.

*Taraxacum japonicum* Koidz. is generally useful for gastroenteric disorders and indigestion and as an antasthenic. In addition, This may act directly upon the pancreas, thereby accelerating the pancreatic functions and improving a decrease in the functions of the digestive system of diabetic patients.

For diabetic patients, an addition of the extract of this plant species to the primary ingredient or component can help activate their gastroenteric functions so as to work in normal conditions, thereby preventing the constipation from occurring and facilitating the urination. In other words, this plant can maximize the action of the major ingredient or component for the treatment of diabetes mellitus in association therewith. A recommended daily dosage preferably may be approximately two grams as the weight of extract. Such an extract in the amount of a daily dosage can be prepared, for example, by immersing five to ten grams of entire portions of the dried plant in an appropriate volume of water.

*Lycium chinense* Mill. may be used for the purpose to effectively prevent an occurrence of arteriosclerotic diseases, such as myocardial infarction, anencephalic infarction, which are one of complications often caused with or associated with diabetes mellitus and which may result from disorders of lipoproteins, i.e. a decrease in high density lipoproteins (HDL cholesterol). It is also useful as an antasthenic and for the acceleration of the liver functions. A recommended daily dosage preferably may be prepared, for example, by immersing six to fifteen grams of the root skin portions of the dried plant in an appropriate volume of water.

*Pueraria lobata* (Willd.) Ohwi may effectively be useful for the treatment of neuralgia and neurotic disorders complicated with diabetes mellitus and accompanied with a pain of the neck, shoulder, joints or head. Further, it may act particularly upon a pain of the legs and an inability or loss of a physical motion. A recommended daily dosage preferably may be prepared, for example, by immersing six grams of the dry root portions of the dried plant in an appropriate volume of water.

*Smilax china* L. may be useful for the treatment of inveterate diapyetic diseases complicated with diabetes mellitus and it is also effective for the alleviation of thirst. As a recommended daily dosage, there may preferably be taken in the form of a liquid prepared, for example, by immersing ten to fifteen grams of the dry root and leaf portions of the dried plant in an appropriate volume of water.

*Lepisorus thunbergianm* (Kaulf.) Ching has the action of treating or curing the infection of the urinary tract and a decrease in the function of the kidney, which may be caused by or associated with diabetes mellitus. Further, it is useful for the urination. The actions of an extract of this plant may serve as lowering high blood glucose levels of diabetic patients, in combination with the actions of the primary ingredient or component of the composition according to the present invention. It is recommended that a diabetic patient preferably takes an extract as a daily dosage, which may be prepared, for example, by immersing two to four grams of the entire portions of the dried plant in an appropriate amount of water.

The vitamins to be added as the secondary ingredient or component may include, for example, vitamin A (an aliphatic acid ester of vitamin A), vitamin $B_i$ (thiamine hydrochloride), vitamin $B_2$ (riboflavin), vitamin $B_6$, vitamin $B_{12}$, vitamin M (folic acid), niacin (nicotinic acid amide) and vitamin E.

A description will be made in more detail of the actions of the secondary ingredient or components to be added to the primary ingredient or component of the composition for treating or curing diabetes mellitus according to the present invention as well as daily dosages which diabetic patients are recommended to take.

Vitamin A is involved with the metabolism of fat and an addition thereof to the primary ingredient or component is considered that it can act indirectly upon a loss of the weight of a diabetic patient. As is well aware, it is of extreme significance for diabetic patients to maintain their body weights at their own standard weight ranges plus or minus ten percent so that the addition thereof serves as decreasing the body weights of the diabetic patients.

Further, the application of the vitamin A in combination with the primary ingredient or component may serve as preventing diabetic patients from causing disorders of the cornea or retina of the eyes of the diabetic patient. For the diabetic patients, as is well known, retinosis is one of the three complications from which the diabetic patients suffer most and it is a No. 1 cause that leads eventually to blindness. It is recommended that an adult male diabetic patient takes at least 2,000 iu daily.

Vitamin $B_1$ is sometimes referred to as an antineuritic vitamin and involved with the metabolism of fat and water. An addition of vitamin $B_1$ to the primary ingredient or component is useful for the treatment or curing of a decrease in power of resistance to diabetes mellitus or complications therewith and the immunological action. Although an aqueous solution of vitamin $B_1$ is very stable, it is less stable to heat so that, when it is added to the primary ingredient or component of the composition for treating or curing diabetes mellitus according to the present invention, care should be paid in storing the preparations containing vitamin $B_1$. A recommended daily dosage for an adult male diabetic patient may preferably be approximately 1.0 mg.

Vitamin $B_2$ may serve as activating the oxidation and reduction of somatic cells and is involved with the metabolism of carbohydrates, particularly glucose, for diabetic patients. This vitamin is also effective for the prevention of an occurrence of disorders or diseases of the eyes which are frequently caused by or associated with diabetes mellitus. A recommended daily dosage for an adult male diabetic patient may preferably be approximately 1.4 mg.

Vitamin $B_6$ is sometimes referred to as a vitamin for anti-dermatitis and may serve as the metabolism of proteins, fats and carbohydrates. An addition of vitamin $B_6$ to the primary ingredient or component may effectively act particularly upon dermatitis that frequently attacks diabetic patients and prevails among them. Further, it is useful for avoidance of amyosthenia and feeling of fatigue or malaise.

Vitamin $B_{12}$ is sometimes referred to as a vitamin for malignant anemia and its addition to the primary ingredient or component may serve as reinforcing power of resistance to diabetes mellitus as well as alleviating inflammation caused particularly by peripheral neuralgia.

Vitamin M (folic acid) may act effectively in association with vitamin $B_{12}$.

Niacin or nicotinic acid amide is deeply involved with the metabolism of glucide as a factor for the prevention of pellagra. An addition of niacin or nicotinic acid amide to the primary ingredient or component may serve as the treatment of diseases resulting from disorders of the metabolism of glucide. A recommended daily dosage for an adult male diabetic patient may preferably be 17 mg.

Vitamin E is referred to as a vitamin for antisterility and its addition to the primary ingredient or component may improve hemokinesis, thereby supplementing the effects to be provided by the primary ingredient or component of the composition for treating or curing diabetes mellitus according to the present invention. A recommended daily dosage for an adult male diabetic patient may preferably be approximately 120 mg.

Chitin and chitosan are both substances of an animal fiber and they are extensively utilized as additives for food. They may be useful for the prevention of arteriosclerosis to be otherwise caused by diabetes mellitus and work in addition to the actions of the primary ingredient or component of the composition for treating or curing diabetes mellitus according to the present invention.

As has been described hereinabove, the composition for treating or curing diabetes mellitus according to the present invention comprises an extract containing the protein polysaccharide as the primary ingredient or component, which is obtained from the genus Tithonia or Ludwigia, as well as the ingredient or component contained in the extract of the different kind of the plant and/or the vitamins and/or chitin and/or chitosan, as needed, to be added thereto as the secondary ingredient or component of the composition for treating or curing diabetes mellitus according to the present invention.

In accordance with the present invention, the extract containing the protein polysaccharide as the primary ingredient or component of the composition for treating or curing diabetes mellitus may be prepared, for example, by immersing a dried material, i.e. leaves, stems, roots or the like, of the plant belonging to the genus Tithonia or Ludwigia in an appropriate solvent at ambient or elevated temperature for an appropriate period of time to extract a protein polysaccharide therefrom and removing the solid material from the solvent to yield an extract which in turn may further be concentrated to an appropriate volume.

More specifically, the extract from the plant belonging to the genus Tithonia may be prepared, for example, by immersing from 50 grams to 200 grams, preferably from 80 grams to 120 grams, of a dry material of the plant in from 500 ml to 5,000 ml of water, concentrating the resulting mixture to 150 ml to 2,000 ml and removing the solid material from the concentrate containing the extract. The extract obtained in the above manner usually contains an amount of extract necessary for a daily dosage so that the extract may be taken as it is as tea or drink or formulated into appropriate forms of preparations.

On the other hand, the extract from the plant belonging to the genus Ludwigia may be prepared, for example, by immersing 100 grams of a dry material of the plant in 1,800 ml of water and boiling the mixture until the mixture is concentrated to approximately 600 ml and removing the solid material from the concentrate containing the extract. The amounts of the plant and/or the solvent may be varied with the amount of the extract expected to be prepared. The extract obtained in the above manner usually contains an amount of extract necessary for a daily dosage so that the extract may be taken as it is as tea or drink or formulated into appropriate forms of preparations.

It is preferred that the composition for treating or curing diabetes mellitus is applied in the form of drink or tea made, for example, by pouring hot water on the plant belonging to the genus Tithonia and/or Ludwigia or by boiling water in which the plant is placed and concentrating the mixture to an appropriate volume.

In addition, the composition for treating or curing diabetes mellitus according to the present invention may be formulated into an appropriate form of preparations for use as medicine. The preparations may be in an form appropriate for use for therapy and such a form may be tablets, pills, pilule, powders, pelvis, granules, capsules, solutions, suspensions, emulsions, injections (for example, solutions or emulsions), suppositories and so on. The preparations may be prepared by formulating the primary ingredient or component contained in the extract from the genus Tithonia or Ludwigia as well as the secondary ingredient or component to be added, as needed, in conventional manner with a pharmacologically acceptable carrier customarily utilized for medicinal purposes, such as, for example, a diluent or recipient, e.g. fillers, connecting agents, disintegrants, humectants, adsorbents, surface active agents, lubricants and so on. In addition, the composition may contain an auxiliary as needed.

It is preferred that the composition for treating or curing diabetes mellitus is applied in the form of drink made, for example, by pouring hot water on the plant belonging to the genus Tithonia and/or Ludwigia or by warming water in which the plant is placed.

In addition, the composition for treating or curing diabetes mellitus according to the present invention may be formulated into an appropriate form of preparations for use as medicine. The preparations may be in an form appropriate for use for therapy and such a form may be tablets, pills, pilule, powders, pelvis, granules, capsules, solutions (i.e. tea or drink), suspensions, emulsions, injections (for example, solutions or emulsions), suppositories and so on. The preparations may be prepared by formulating the primary ingredient or component contained in the extract from the genus Tithonia or Ludwigia as well as the secondary ingredient or component to be added, as needed, in conventional manner with a pharmacologically acceptable carrier customarily utilized for medicinal use, such as, for example, a diluent or recipient, e.g. fillers, connecting agents, disintegrants, humectants, adsorbents, surface active agents, lubricants and so on. In addition, the composition for treating or curing diabetes mellitus may contain an auxiliary as needed.

In accordance with the present invention, the carrier to be used for the formulation of the composition for treating or curing diabetes mellitus may be any pharmacologically acceptable substance or material customarily utilized for the formulation of the preparations for medicinal use. Representatives of such carriers may be recipients such as, for example, lactose, sugar, glucose, urea, starch, calcium carbonate, sodium chloride, crystalline cellulose, silicic acid and so on; connecting agents such as, for example, water, an alcohol, e.g. ethanol etc., gelatine solution, methyl cellulose, carboxymethyl cellulose, potassium phosphate, polyvinyl pyrrolidone, and so on; disintegrants such as, for example, agar powder, starch, sodium hydrogen carbonate, calcium carbonate, an polyoxy ethylene sorbitan fatty acid ester, sodium lauryl sulfate, stearic acid monoglyceride and so on; humectants such as, for example, glycerin, starch, and so on; adsorbents such as, for example, starch, lactose, kaolin, bentonite, colloidal silicic acid and so on; and lubricants such as, for example, stearic acid salt, purified talc, boric acid powder, polyethylene glycol and so on. The auxiliaries may also be any pharmacologically acceptable substance or material customarily utilized for medicinal use. Representatives of such auxiliaries may be, for example, thickeners, antioxidants, absorption accelerators, absorption suppressors, crystallization inhibiting agents, complexing agents, isotonic agents, wettable powders, and so on. To the composition for treating or curing diabetes mellitus according to the present invention, as needed, there may be added, for example, dissolution aids, buffers, analgesic agents, colorants, preservatives, perfumes, sweeteners, and so on.

The composition for treating or curing diabetes mellitus according to the present invention can be formulated with the appropriate carriers into tablets in conventional manner. Further, the tablets may be coated on their surfaces with a coating to thereby form sugar-coated tablets, gelatine-coated tablets, enteric-coated tablets, film-coated tablets, two-ply tablets, multi-ply tablets, and so on. The composition for treating or curing diabetes mellitus can also be formulated with the appropriate carriers into pills or pilule in conventional manner. As the carriers appropriate for the formulation of the composition for treating or curing diabetes mellitus into the tablets or pills or pilule, there may be mentioned, for example, recipients such as, e.g. glucose, lactose, starch, kaolin, talc, cacao butter, hardened vegetable oils and so on; connecting agents such as, e.g. ethanol, gelatine, tragacanth gum powders, gum arabic and so on; and disintegrants such as, e.g. laminaran agar and so on. In addition, the composition for treating or curing diabetes mellitus may be conventionally formulated into powders, pelvis, granules or capsules in substantially the same manner as into the tablets or pills or pilule.

Furthermore, the composition for treating or curing diabetes mellitus may be formulated into solutions, suspensions or emulsions in conventional manner. Particularly, when the composition is formulated in the form of drink or tea, it may be prepared, for example, by warming water containing an appropriate volume of the plant from which an extract is to be extracted in a solvent and concentrating the mixture to an appropriate volume. When the composition is prepared in the form of solutions, suspensions or emulsions, there may be utilized diluents customarily employed in this field. Such diluents may include, for example, water, ethyl alcohol, propylene alcohol, isostearyl alcohol, a polyoxyethylene sorbitan fatty acid ester and so on. The such compositions may also be made isotonic, as needed, by adding sodium chloride, glucose, glycerin or the like to the liquid preparations. In addition, the composition for treating or curing diabetes mellitus may be formulated with the diluents as illustrated hereinabove into injections in the form of a solution or emulsion. In formulating the composition into such injections, it is preferred that an acid such as methane sulfonic acid, propionic acid, hydrochloric acid, succinic acid or the like be added, as needed, in order to cause the active ingredient or component to fail to precipitate or sediment in the liquid preparations. Further, when the composition for treating or curing diabetes mellitus is applied in the form of liquid preparations, it is preferred that a pH of the liquid preparations be adjusted to an appropriate range, as needed, by adding an acid such as hydrochloric acid or sulfuric acid or an alkali such as sodium hydroxide.

When the composition for treating or curing diabetes mellitus is formulated into suppositories, there may be utilized carriers customarily employed in the field of the preparation of suppositories. Such carriers may include, for example, polyethylene glycol, a higher alcohol or its ester, cacao butter, gelatin, semi-synthetic glyceride and so on.

The composition for treating or curing diabetes mellitus may be administered in various routes of administration and, although the route of administration of the composition is not limited to a particular one, it is preferred that it is varied appropriately with the form of the preparations, the extent of the symptoms of patients and so on. When the composition is administered in the form of preparations such as, for example, tablets, pills, pilule, powders, pelvis, granules, capsules, solutions, suspensions or emulsions, it is preferred that it is administered orally. When the composition is administered in the form of preparations such as, for example, injections, e.g. solutions or emulsions, it is preferred that it is administered intravenously although it can be administered, as needed, through intradermal or subcutaneous routes. On the other hand, when the composition is administered in the form of preparations, such as suppositories, it is administered through rectal routes. These routes of administration are conventional in itself.

The composition for treating or curing diabetes mellitus prepared in the manner as described hereinabove may be appropriately applied to patients with diabetes mellitus in various ways in accordance with the form of the composition, the route of administration, the age and sex of patients, the extent of the symptoms of patients and so on. The composition may be applied at one time or in installments. A daily dosage may be varied with the kind of the extract obtained from the plant belonging to the genus Tithonia or Ludwigia as well as with the form of the composition, the route of administration, the age and sex of patients, the extent of the symptoms of patients and so on. The daily dosage may range from approximately 15 grams to 30 grams, preferably from approximately 20 grams to 25 grams, more preferably from 23 grams to 24 grams as the weight of an extract obtained particularly from the plant belonging to the genus Tithonia. On the other hand, the daily dosage may range from approximately 12 grams to 20 grams, preferably from approximately 14 grams to 16 grams, as the weight of an extract obtained particularly from the plant belonging to the genus Ludwigia.

The composition for treating or curing diabetes mellitus according to the present invention may be administered in a variety of conventional ways and the way of administration of the composition is not limited to a particular one. For example, the composition may be administered for an appropriate period of time ranging over several months, a composition containing as the primary ingredient or component an extract or extract obtained from the plant or plants belonging to the genus Tithonia and/or Ludwigia or containing a combination of the primary ingredient or component with the secondary ingredient or component or a combination of the primary ingredient or component with the vitamin and/or chitin and/or chitosan or a combination of the primary and secondary ingredients or components with the vitamin and/or chitin and/or chitosan. It is also possible to administer a composition having a different ingredient or component for a certain period of time after administration of the composition as illustrated hereinabove. More specifically, the composition is first administered for a certain period of time, for example, for approximately two to three months, which contains the primary ingredient or component to which there is or are added the secondary ingredient or component and/or the vitamin and/or chitosan and/or chitin and another composition is then administered for a certain period of time ranging, for example, over approximately one month, which contains a different kind of the primary ingredient or component to which a different kind or the identical kind of the secondary ingredient or component and/or vitamin and/or chitosan and/or chitin. Preferably, there is first administered a composition containing an extract obtained from the plant belonging to the genus Tithonia for a period of time ranging from approximately one to three months and there is thereafter administered a composition containing an extract obtained from the plant belonging to the genus Ludwigia for a period of time prefer-ably shorter than the period of time during which the composition containing the extract from the plant of genus Tithonia, e.g. for approximately one month. These ways of administration are described merely for illustrations and a variety and a great number of other combinations are likewise to be understood as included in the scope of the present invention.

Although the composition for treating or curing diabetes mellitus can be stored in conventional manner, it is preferred to store it in a cold place particularly when it is stored in the form of an extract or liquid preparations. On the other hand, the composition for treating or curing diabetes mellitus in the form of solid preparations can be stored in a conventional fashion for a longer period of time. When the composition for treating or curing diabetes mellitus is stored in the form of such an extract or liquid preparations, it is recommended that it is stored in a cold place in an amount corresponding to two to three daily dosages in order to cause no precipitation of effective ingredients contained therein during storage.

When the composition for treating or curing diabetes mellitus is applied in the form of tea or drink, it is preferred that it is drunken mainly during hunger or during a period of time between meals. Further, attention is to be paid to the fact that diabetic patients should not eat radish during a period of administration because there is the risk that some ingredients of radish might alleviate the performance of the composition for treating or curing diabetes mellitus according to the present invention, thereby failing to achieve the desired effects to be otherwise expected by the composition.

A description now will be made of the specific embodiments of the present invention by way of examples.

Example No. 1

Stems and leaves of a plant, i.e. *Tithonia diversifolia* (Hemsl.) A. Gray, were dried well and cut into small pieces. The small pieces of the dried stems and leaves of the plant in the amount of 180 grams were poured into 3,000 ml of water and the mixture was heated at high temperature until it became boiled, followed by lowering the temperature to some extent and heating it until the mixture was concentrated to about 1,000 ml. The mixture was then filtered and the entire weight of the residue was again poured in 600 ml of water and heated until the mixture was concentrated to about 200 ml. The first and second concentrates were combined to give a total weight of about 1,200 ml of the extracted solution which in turn contained approximately 42 grams as the weight of an extract.

Example No. 2

A total weight of 75 grams of small pieces of dried stems and leaves of a plant, i.e. *Ludwigia octovalvis* Raven, was poured into 800 ml of water and the mixture was concentrated to about 400 ml. The concentrate was then filtered to give an extract. On the other hand, the residue was poured again in 400 ml of water and the mixture was heated until it was concentrated to 200 ml. The two portions of the extracts were combined for drinking tea as a daily dosage.

Example No. 3

An extract from a plant, i.e. *Ludwigia prostrata* Roxb. or *Ludwigia epilobioides* Maxim, was prepared in substantially the same manner as in Example No. 2.

Example No. 4

An extract from a plant, i.e. *Tithonia rotundifolia* (Mill) Blake, was prepared in substantially the same manner as in Example No. 1.

Example No. 5

A total weight of 100 grams of a plant, i.e. *Tithonia diversifolia* (Hemsl.) A. Gray, and a total weight of 20 grams of small pieces of dried barks and roots of the plant, i.e. Aralia elata Seemann, were poured into 3,000 ml and the resulting mixture was boiled at 100 C until it became concentrated to approximately 1,000 ml. The resulting mixture was filtered, thereby removing the solid residue and yielding a filtrate containing an extract.

Example No. 6

A total weight of 100 grams of the plant, i.e. *Ludwigia octovalvis* Raven and a total weight of 20 grams of small pieces of dried cut barks and roots of the plant, i.e. *Aralia elata* Seemann, were poured into 1,800 ml and the resulting mixture was boiled at 100° C. until it became concentrated to about one third of the original amount of the mixture, i.e. to approximately 600 ml. The resulting mixture was filtered, thereby removing the solid residue and yielding a filtrate containing an extract.

Example No. 7

Roots of a plant, i.e. *Rerhmannia glutinosa* Libosch. var. purpurea Makino, were poured in water and the resulting mixture was boiled and concentrated, thereby yielding approximately 5 grams of an extract as *Rerhmanniae radix*.

An entire weight of the extract was formulated with a total weight of 23 grams of the extract prepared as in Example No. 1 to give a daily dosage of the composition.

Example No. 8

Roots of the plant, i.e. *Rerhmannia glutinosa* Libosch. var. purpurea Makino, were poured in water and the resulting mixture was boiled and concentrated in substantially the same manner as in Example No. 7, thereby yielding approximately 5 grams of an extract as *Rerhmanniae radix*.

An entire weight of the extract was formulated with a total weight of 14 grams of the extract prepared as in Example No. 3 from the plant (i.e. *Ludwigia prostrata* Roxb. and *Ludwigia epilobioides* Maxim) to thereby give a daily dosage of the composition.

Example No. 9

A total weight of 100 grams of the plant, i.e. *Tithonia rotundifolia* (Mill) Brake, and a total weight of 15 grams of small pieces of dried roots of a plant, i.e. *Panax ginseng* C. A. Meyer, were poured into 1,800 ml and the resulting mixture was boiled at 100° C. until it became concentrated to about approximately 1,000 ml. The resulting mixture was filtered, thereby removing the solid residue and yielding a filtrate containing an extract.

Example No. 10

A total weight of 100 grams of the plant, i.e. *Ludwigia octovalvis* Raven, and a total weight of 15 grams of small pieces of dried roots of the plant, i.e. *Panax ginseng* C. A. Meyer, were poured into 1,800 ml and the resulting mixture was boiled at 100° C. until it became concentrated to about approximately 600 ml. The resulting mixture was filtered, thereby removing the solid residue and yielding a filtrate containing an extract.

Example No. 11

To 20 grams of the extract from the plant, i.e. *Tithonia rotundifolia* (Mill) Brake, was added 4 grams of an extract obtained from a plant, i.e. *Trichosanthes kirilowii* Maxim., thereby formulating the composition in the amount of a daily dosage. The extract of the plant was prepared in substantially the same manner as in Example No. 7 in which the extract of the plant, i.e. *Rerhmannia glutinosa* Libosch. var. purpurea Makino, were prepared.

Example No. 12

The plant, i.e. *Ludwigia prostrata* Roxb. or *Ludwigia epilobioides* Maxim, was extracted in substantially the same manner as in Example No. 2 to thereby yield an extract.

A total weight of 14 grams was formulated with 4 grams of an extract prepared as in Example No. 11 from the plant, i.e. *Trichosanthes kirilowii* Maxim, into the composition in the amount of a daily dosage.

Example No. 13

A formulation for treating diabetes mellitus was prepared in the amount of a daily dosage by combining 24 grams of the extract from the plant, i.e. *Tithonia diversifolia* (Hemsl.) A. Gray, 5 grams of the extract prepared as in Example No. 7 from the plant, i.e. *Rerhmannia glutinosa* Libosch. var. purpurea Makino, and 3 grams of an extract prepared from a plant, i.e. *Schizandra chinensis* (Turcz) Baill. The extract of the plant, i.e. *Schizandra chinensis* (Turcz) Baill, was prepared in substantially the same manner as in Example No. 7.

Example No. 14

A daily dosage of a formulation for treating diabetes mellitus was prepared by combining 24 grams of the plant, i.e. *Ludwigia octovalvis* Raven, 5 grams of the extract of *Rerhmanniae radix* and 3 grams of the extract prepared from the plant, i.e. *Schizandra chinensis* (Turcz) Baill.

As have been described hereinabove, the specific embodiments of the compositions for treating diabetes mellitus according to the present invention are directed to those which contains the extract prepared from the plant belonging to either of the genus Tithonia or Ludwigia as the primary ingredient or component to which the secondary ingredient or component is added as needed. As another embodiments of the compositions for treating diabetes mellitus according to the present invention, there may be used, for example, compositions containing a plurality of extracts prepared from the plants of the identical genus, Tithonia or Ludwigia, containing a combination of extracts prepared from the plants of the different genus, Tithonia and Ludwigia. To each of the compositions containing a plurality of such extracts, there may be added a plurality of the secondary ingredients or components.

Further, the primary and/or secondary ingredients or components may be formulated, for example, in the form of an extract, powder, drink or tea. In addition, the vitamins or chitin or chitosan may be added preferably to the primary or secondary ingredient or component in the form of an extract.

Now, a description will be made of cases in which the composition for treating diabetes mellitus according to the present invention is applied to patients suffering from diabetes mellitus. In these cases, the diabetic patients were administered with the composition containing the extract prepared from the plant belonging to the genus, Tithonia, for an appropriate period of time and thereafter with the composition containing the extract prepared from the plant belonging to the genus, Ludwigia, for an appropriate period of time yet shorter than the period of time during which the composition containing the extract from the plant of the genus Tithonia has been administered.

Case No. 1

A diabetic patient was suffering from malaise, polyuria, thirst and polyphagia as subjective symptoms prior to testing. Further, the patient demonstrated laboratory test results of urine glucose (+++); a number of white blood cells (WBC) in urine residue of 15–25/HPF; WBC of 11,800 per cm; and blood glucose: 226 mg/dl at AC and 459 mg/dl at PC (2 hours after meal).

The diabetic patient was administered with 600 ml of the composition prepared in Example No. 1 in several installments during hunger between meals and the administration was continued for two months. In nearly one month after administration, various symptoms of the diabetic patient were improved to a considerable extent and the subjective symptoms of the patient have disappeared in two months after administration.

After the completion of the administration of the extract from the plant, i.e. *Tithonia diversifolia* (Hemsl.) A. Gray, the extract prepared in Example No. 2 from the plant, i.e. *Ludwigia octovalvis* Raven, was continuously administered in several installments during hunger for an additional one month.

At the time when the above compositions were administered for a total period of three months, the diabetic patient had no various subjective symptoms and demonstrated laboratory test results as follows: urine glucose (–); a number of white blood cells (WBC) in urine residue of 2 to 4/HPF; WBC of 10,000 per cmm; and blood glucose of 88 mg/dl at AC and 155 mg/dl at PC (2 hours after meal).

In three months after administration of the composition containing the extract from *Ludwigia octovalvis* Raven, the patient still had no various subjective symptoms and demonstrated laboratory test results as follows: urine glucose (–); a number of white blood cells (WBC) in urine residue of 1 to 2/HPF; and blood glucose of 62 mg/dl at AC and 96 mg/dl at PC (2 hours after meal).

Further, in four months after administration of the composition containing the extract from *Ludwigia octovalvis* Raven, the patient still had no various subjective symptoms and demonstrated laboratory test results as follows: urine glucose (–); a number of white blood cells (WBC) in urine residue of 0 to 2/HPF; and blood glucose of 79 mg/dl at AC and 111 mg/dl at PC (2 hours after meal).

It is further found at this moment of time that an infection of the urinary tracts as a complication caused by or associated with diabetes mellitus was cured completely.

In four years after the completion of administration of the extract from *Ludwigia octovalvis* Raven, the patient was subjected to laboratory tests. At this moment of the test, the patient did not suffer from any subjective symptoms and demonstrated laboratory test results as follows: urine glucose (–); and blood glucose of 97 mg/dl at AC and 140 mg/dl at PC (2 hours after meal).

In this case, the patient was forced to carry out great intemperance for one week prior to the test, in order to ensure a potential recurrence of diabetes mellitus.

It was found as a result of the test that there was no risk of a potential reoccurrence of diabetes mellitus as long as the extract from *Ludwigia octovalvis* Raven has been administered continuously after the completion of the administration of the extract from *Tithonia diversifolia* (Hemsl.) A. Gray.

It can be noted, however, that although the administration of the extract prepared from the plant of the genus, Tithonia, caused the various symptoms to temporarily disappear or diminish for a certain period of time, diabetes mellitus is caused to reoccur unless the extract or drink prepared from the plant, Ludwigia, has been administered continuously after the administration of the extract from the plant of the genus, Tithonia.

Case No. 2

A diabetic patient was administered first with 23 grams of the extract from the plant (*Tithonia diversifolia* (Hemsl.) A. Gray) prepared in Example No. 1 for a period of two months and thereafter with 14 grams of the extract from the plant (*Ludwigia octovalvis* Raven) prepared in Example No. 2 for a period of one month in substantially the same manner as in Case No. 1.

The test results are shown in Table 1 below.

TABLE 1

| | | PERIOD AFTER ADMINISTRATION | | | | | | |
|---|---|---|---|---|---|---|---|---|
| | DAY 1 | 2 MONTH | 3 MONTH | 4 MONTH | 5 MONTH | 6 MONTH | 8.5 MONTH | 10 MONTH |
| I | 149 | 107 | 96 | 91 | 82 | 96 | 82 | 76 |
| II | 156 | 122 | 127 | 122 | 96 | 117 | 115 | 104 |
| III | 243 | 169 | 122 | 126 | 103 | 125 | 191 | 114 |
| IV | 7.3 | 5.8 | 5.8 | — | 5.8 | 6.1 | 5.8 | 5.2 |

In Table 1 above, the column on the left end side means the blood glucose levels in which the row "I", indicates the blood glucose levels in serum at AC; the row "II" indicates the blood glucose levels in blood at AC (prior to load by glucose); the row "III" indicates the blood glucose levels in blood in 120 minutes after meal; and the row "IV" indicates the values of HbA1c.

The test results are further shown in FIG. 1 for ready reference. In FIG. 1, the solid line connected by symbols as indicated by square marks refers to the blood glucose levels as observed at the row I of the Table 1 above; the solid line connected by symbols indicated by diamond-shaped marks refers to the blood glucose levels as observed at the row II of the Table 1 above; and the solid line connected by symbols indicated by round marks refers to the blood glucose levels as observed at the row III of the Table 1 above.

Case No. 3

A diabetic patient was administered first with the extract from the plant (*Tithonia diversifolia* (Hemsl.) prepared in Example No. 1 for the period of two months and thereafter with the extract from the plant (*Ludwigia octovalvis* Raven) prepared in Example No. 2 for the period of one month in substantially the same manner as in Case No. 1.

The test results are shown in Table 2 below.

TABLE 2

| | | PERIOD AFTER ADMINISTRATION | | | | | | |
|---|---|---|---|---|---|---|---|---|
| | DAY 1 | 3 MONTH | 4.5 MONTH | 5.5 MONTH | 6.5 MONTH | 7.5 MONTH | 9.5 MONTH | 11 MONTH |
| I | 219 | 195 | 179 | 191 | — | — | — | — |
| II | 240 | — | 216 | 181 | 212 | 125 | 133 | 102 |
| III | 351 | — | 364 | 310 | 368 | 274 | 249 | 213 |
| IV | 463 | — | 374 | 205 | 336 | 258 | 244 | 233 |
| V | 9.5 | — | 8.4 | 7.8 | 7.9 | 6.5 | 6.9 | 6.7 |

In Table 1 above, the column on the left end side means the blood glucose levels in which the row "I" indicates the blood glucose levels in serum at AC; the row "II" indicates the blood glucose levels in blood at AC (prior to load by glucose); the row "III" indicates the blood glucose levels in blood in 60 minutes after meal; the row "IV" indicates the blood glucose levels in blood in 120 minutes after meal; and the row "V" indicates the values of HbA1c.

The test results as indicated in the rows I, III and IV of Table 2 above are shown in FIG. 2, in which the test results as indicated in the row I are referred to by square marks, those in the row III by diamond-shaped marks, and those in the row IV by round marks.

Case No. 4

A diabetic patient was administered first with the extracts from the plants (*Tithonia rotundifolia* (Mill) Blake) prepared in Example No. 4 for a period of two months and thereafter with the extract from the plant (*Ludwigia prostrata* Roxb. or *Ludwigia epilobioides* Maxim) prepared in Example No. 3 for a period of one month in substantially the same manner as in

Case No. 1.

The test results are shown in Table 3 below.

TABLE 3

| | | PERIOD AFTER ADMINISTRATION | | | | |
|---|---|---|---|---|---|---|
| | DAY 1 | 1 MONTH | 2 MONTHS | 3 MONTHS | 5 MONTHS | 6 MONTHS |
| I | 184 | — | 182 | 173 | 155 | — |
| II | 221 | 188 | 213 | 205 | 192 | 97 |
| III | 347 | 344 | 372 | — | — | — |
| IV | 406 | 352 | 460 | — | — | — |
| V | 463 | 379 | — | — | — | — |
| VI | 453 | 342 | 391 | 208 | 246 | 172 |
| VII | 11.4 | 9.6 | 9.6 | 9.3 | 8.8 | — |

In Table 1 above, the column on the left end side means the blood glucose levels in which the row "I" indicates the blood glucose levels in serum at AC; the row "II" indicates the blood glucose levels in blood at AC (prior to load by glucose); the row "III" indicates the blood glucose levels in blood in 30 minutes after meal; the row "IV" indicates the blood glucose levels in blood in 60 minutes after meal; the row "V" indicates the blood glucose levels in blood in 90 minutes after meal; the row "VI" indicates the blood glucose levels in blood in 120 minutes after meal; and the row "VI" indicates the values of HbA1c.

The test results as indicated in the rows I, II and VI of Table 2 above are shown in FIG. 2, in which the test results as indicated in the row I are referred to by square marks, those in the row II by square marks, and those in the row VI by round marks.

Case No. 5

A diabetic patient was administered with the extracts from the plants (*Tithonia diversifolia* (Hemsl.) A. Gray and *Aralia elata* Seeman) prepared in Example No. 5 in the form of drink or tea for two months and then with the extracts from the plants (*Ludwigia octovalvis* Raven and *Aralia elata* Seeman) prepared in Example No. 6 in the form of drink or tea for one month immediately after the completion of administration of the extract of Example No. 5.

At the time of the start of the test, the diabetic patient, 155 cm in height and 70 kilograms in weight, had a variety of subjective symptoms as follows: a remarkably severe extent of malaise, numbness at the part of the legs below the thighs, numbness and a pain at the part of the great toes of the feet, polyuria, thirst and polyphagia. Laboratory test results for the diabetic patient for testing were shown as follows: urine glucose (−); proteins (±); blood glucose: 270 mg/dl at AC and 309 mg/dl at PC (2 hours after meal); GOT: 90 iu/l; GPT: 114 iu/l; and γ-GTP: 297 mu/ml.

The extracts prepared in Example No. 5 was administered in the form of tea or drink daily at several times during hunger between meals for two months. After two months have elapsed, the diabetic patient no longer felt any subjective symptoms.

After the completion of administration of the composition containing a combination of the extracts of the plants (*Tithonia diversifolia* (Hemsl.) A. Gray and *Aralia elata* Seeman) for two months, the diabetic patient was continuously administered with the composition containing a combination of the extracts of the plants (*Ludwigia octovalvis* Raven and *Aralia elata* Seeman) for another one month.

At the time of an elapse of a total period of three months from the start of administration, the diabetic patient had no longer any subjective symptoms and felt very good. Laboratory test results further indicate that urine glucose was negative; proteins were negative; blood glucose was at the rate of 128 mg/dl at AC and 222 mg/dl at PC (2 hours after meal); GOT was 33 iu/l; GPT was 42 iu/l; and γ-GTP was 169 mu/ml.

At the time when two months have elapsed after the completion of administration of the combination of the extracts of the plants (*Ludwigia octovalvis* Raven and *Aralia elata* Seeman), the diabetic patient had no subjective symptoms and demonstrated laboratory test results as follows: urine glucose: (−); proteins: (−); blood glucose: 134 mg/dl at AC and 194 mg/dl at PC (2 hours after meal); GOT: 27 iu/l; GPT: 34 iu/l; and γ-GTP: 45 mu/ml.

Further, at the time when three months have elapsed after the completion of administration of the combination of the extracts of the plants (*Ludwigia octovalvis* Raven and *Aralia elata* Seeman), the diabetic patient had no subjective symptoms and demonstrated laboratory test results as follows: urine glucose: (−); blood glucose: 71 mg/dl at AC and 142 mg/dl at PC (2 hours after meal); GOT: 24 iu/l; GPT: 28 iu/l; and γ-GTP: 48 mu/ml.

It was further found that the liver functions were working in normal ways and diabetes mellitus was considered to have been cured. Additionally, it was found that chronic hepatitis was also cured thoroughly. This healthy condition was maintained thereafter.

Case No. 6

This is concerned with a case in which an extract from the plant (*Rerhmannia glutinosa* Libosch. var. *purpurea* Makino) was added to each of the extracts from the plants (*Tithonia diversifolia* (Hemsl.) A. Gray and *Ludwigia prostrata* Roxb. or *Ludwigia epilobioides* Maxim) and the combination of the extract from the plant (*Rerhmannia glutinosa* Libosch. var. *purpurea* Makino) with the extract from the plant (*Tithonia diversifolia* (Hemsl.) A. Gray) was first administered for two months, followed by administration of the composition containing the extracts of the plants (*Ludwigia prostrata* Roxb. or *Ludwigia epilobioides* Maxim and *Rerhmannia glutinosa* Libosch. var. *purpurea* Makino) for another one month.

A diabetic patient, 166 cm in height and 70 kilograms in weight, was administered first with the composition prepared in Example No. 7 containing a combination of the extracts of the plants (*Tithonia diversifolia* (Hemsl.) A. Gray and *Rerhmannia glutinosa* Libosch. var. *purpurea* Makino) for two months and then with the composition prepared in Example No. 8 containing a combination of the extracts of the plants (*Ludwigia prostrata* Roxb. or *Ludwigia epilobioides* Maxim and *Rerhmannia glutinosa* Libosch. var. *purpurea* Makino) for another one month.

Prior to testing, the diabetic patient had subjective symptoms as follows: dimness of sight, feeling of fatigue or malaise, polyuria, thirst and nervous disorders such as convulsions of the lower limbs and numbness of the legs. Laboratory test results indicate that urine glucose was positive (++); GOT was 22 iu/l; GPT was 18 iu/l; γ-GTP was 56 mu/ml; LDH was 331 iu/l; the rate of neutral fats was 267 mg/dl. Further, tests for blood glucose were conducted under load by applying 50 grams of glucose and test results were indicated as follows: 180 mg/dl before glucose load; 360 mg/dl in 60 minutes after glucose load; 263 mg/dl in 120 minutes after glucose load; and 188 mg/dl in 180 minutes after glucose load.

After administration of the composition containing the extracts of the plants (*Tithonia diversifolia* (Hemsl.) A. Gray and *Rerhmannia glutinosa* Libosch. var. *purpurea* Makino) for two months, the diabetic patient was subjected to laboratory tests. The patient no longer perceived any subjective symptoms but a slight extent of dimness of sight. In other words, feeling of fatigue or malaise disappeared; no thirst was felt any longer; and the extent of nervous disorders disappeared to a remarkable extent. Further, the laboratory test indicates remarkable improvements in its results in such a fashion that urine glucose was still positive but reduced to (+); the rates of blood glucose under glucose load were lowered to a remarkably great extent to 121 mg/dl prior to glucose load; 183 mg/dl in 60 minutes after glucose load; 130 mg/dl in 120 minutes after glucose load; and 127 mg/dl in 180 minutes after glucose load.

Thereafter, the diabetic patient was administered with the composition prepared in Example No. 8 for another one month. After the completion of administration of the second composition for one month, the subjective symptoms were improved greatly and laboratory test results indicate great improvements. The patient no longer suffered from any subjective symptoms. The test results are as follows: urine glucose (−); 88 mg/dl prior to glucose load; 105 mg/dl in 60 minutes after glucose load; and 92 mg/dl in 120 minutes after glucose load; GOT: 20 iu/l; GPT: 19 iu/l; and neutral fats: 152 mg/dl.

It is to be noted herein that a slightly delayed decrease in the blood glucose level prior to glucose load indicates that it is less possible to cause the blood glucose level to become too low.

As two months have passed after the end of administration of the combined extracts of the plants (*Ludwigia prostrata* Roxb. or *Ludwigia epilobioides* Maxim and *Rerhmannia glutinosa* Libosch. var. *purpurea* Makino), the diabetic patient was subjected to subjective symptoms and laboratory tests. As a result, it was found that the patient no longer felt any subjective symptoms whatsoever and the test results were maintained even with no or little changes of the status of urine glucose and rates of blood glucose under glucose load. The blood glucose rates were 74 mg/dl prior to glucose load and 98 mg/dl in 60 minutes after glucose load. The patient weighed 68.5 kilograms and kept a good shape although a decrease in the body weight is low.

Case No. 7

This is concerned with a case in which, as the first composition, tea or drink containing an extract from the plant (*Panax ginseng* C. A. Meyer) was added to each of the extracts from the plants (*Tithonia rotundifolia* (Mill) Blake and *Ludwigia octovalvis* Raven) and the combination of the extract from the plant (*Panax ginseng* C. A. Meyer) with the extract from the plant (*Tithonia rotundifolia* (Mill) Blake was first administered for two months, followed by administration of the composition containing the extracts of the plants (*Ludwigia octovalvis* Raven and *Panax ginseng* C. A. Meyer) for another one month.

A diabetic patient, 169 cm in height and 68 kilograms in weight, was administered with the first composition containing the combination of the extract from the plant (*Tithonia rotundifolia* (Mill) Blake with the extract from the plant (*Panax ginseng* C. A. Meyer) for two months by drinking a daily dosage of 1,000 ml as tea in several installments in a similar manner as in Case No. 3.

Before testing, the diabetic patient perceived subjective symptoms as follows: nervous disorders such as, for example, numbness and abnormal feeling on the hands and legs; likelihood to cause diarrhea or constipation; likelihood to cause suppuration; feeling heavy on the legs without doing anything; thirst; and polyphagia.

Laboratory test results were as follows: urine glucose: (−); blood glucose by application load of glucose of 75 grams: 122 mg/dl before glucose load; 196 mg/dl in 30 minutes after glucose load; 239 mg/dl in 60 minutes after glucose load; and 244 mg/dl in 120 minutes after glucose load; GOT: 23 iu/l; GPT: 24 iu/l; LDH: 297 iu/l; γ-GTP: 92 mu/ml; HDL cholesterol: 38 mg/dl; and neutral fats: 182 mg/dl.

After the completion of administration of the first composition as tea in two months, the subjective symptoms and laboratory test results have been improved to a great extent. The diabetic patient still had some degree of nervous disorders; however, the patient felt no longer numbness on the thighs and no thirst. Laboratory test results indicate that urine glucose was negative; and the blood glucose levels under load of 75 grams of glucose were reduced to 120 mg/dl before glucose load; 162 mg/dl in 60 minutes after glucose load; and 155 mg/dl in 120 minutes after glucose load.

Thereafter, the patient was continuously administered with the second composition containing the combined extracts of the plants (Ludwigia octovalvis Raven and Panax ginseng C.A. Mayer) as tea, prepared in Example No. 10 above, for another one month.

After the one-month administration of the second composition, the patient was subjected to investigations for subjective symptoms and laboratory test. The patient no longer had any subjective symptoms and indicated negative urine glucose. The laboratory test results indicate further improvements such that the blood glucose levels under load of 75 grams of glucose were lowered to 82 mg/dl before glucose load; 128 mg/dl in 60 minutes after glucose load; and 98 mg/dl in 120 minutes after glucose load.

In two months after the completion of administration of the second composition, the diabetic patient was investigated again for subjective symptoms and laboratory tests. The diabetic patient did not perceive any subjective symptoms. The laboratory test results show that urine glucose still remained negative and the blood glucose levels under glucose load by applying 75 grams of glucose indicate 79 mg/dl before glucose load; 131 mg/dl in 60 minutes after glucose load; and 97 mg/dl in 120 minutes after glucose load.

From the foregoing laboratory test results, it is considered that the patient was in an interim state of diabetes mellitus between the limit area and the diabetes mellitus area.

Case No. 8

This is concerned with a case in which tea or drink containing an extract from the plant (Trichosanthes kirilowii Maxim) was added to each of the extracts from the plants (Tithonia rotundifolia (Mill) Blake and Ludwigia prostrata Roxb. or Ludwigia epilobioides Maxim) and the first composition containing the combination of the extract from the plant (Trichosanthes kirilowii Maxim) with the extract from the plant (Tithonia rotundifolia (Mill) Blake) was first administered for two months, followed by administration of the second composition containing the combined extracts of the plants (Ludwigia prostrata Roxb. or Ludwigia epilobioides Maxim and Trichosanthes kirilowii Maxim) for another one month.

A diabetic patient, 153 cm in height and 65 kilograms in weight, was first administered with the first composition prepared in Example No. 11 for two months. The amount of meal was limited to a half of a healthy person during this testing.

The diabetic patient had subjective symptoms such as a remarkably high extent of thirst, polydipsia, polyphagia, malaise, polyuria, and disorders of the motorium and the esthesic nerves of the legs. Laboratory test results were as follows: urine glucose: (++); blood glucose levels under glucose load by applying 75 grams of glucose: 320 mg/dl before glucose load, 500 mg/dl in 60 minutes after glucose load, and 421 mg/dl in 120 minutes after glucose load; GOT: 12 iu/l; GPT: 15 iu/l; LDH: 277 iu/l; HbA1c: 8.6; and neutral fat: 93 mg/dl.

After the two-month administration of the first composition, the subjective symptoms were changed to a decrease in an extent of thirst; no malaise; and a decrease in an extent of the disorders of the motorium of the legs. Although the urine glucose was still positive (++), the laboratory test results of the blood glucose levels under glucose load by applying 75 grams of glucose were lowered to 240 mg/dl at AC before glucose load, 261 mg/dl in 60 minutes after meal, and 246 mg/dl in 120 minutes after meal. Further, the other test items did not change to a great extent as follows: GOT: 13 iu/l; GPTs 18 iu/l; LDH: 265 iu/l; HbA1c: 8.5; and neutral fat: 81 mg/dl.

After the completion of administration of the first composition for two months, the diabetic patient was continuously administered with the second composition prepared in Example No. 12 for another one month.

After one month during which the second composition was administered, the diabetic patient was subjected to investigations for subjective symptoms and laboratory tests. The diabetic patient no longer felt any thirst and had no other symptoms. The laboratory test results were as follows: urine glucose: (+); blood glucose levels: 176 mg/dl at AC, 192 mg/dl in 60 minutes after meal, and 196 mg/dl in 120 minutes after meal; HbA1c: 7.9; and neutral fat: 79 mg/dl.

Further, the diabetic patient was subjected to investigations for subjective symptoms and laboratory tests in two months after the completion of administration of the second composition. The diabetic patient lost weight to 57 kilograms and had no subjective symptoms. The laboratory test results were as follows: urine glucose: (−); blood glucose levels: 97 mg/dl at AC, and 126 mg/dl in 120 minutes after meal; HbA1c: 6.4; and neutral fat: 77 mg/dl. As a result, the diabetic patient had no desire to drink water and the amount of meal was increased gradually to a normal amount a healthy person could take.

The cases as described hereinabove are those where the first composition containing the extract of the plant belonging to the genus Tithonia was first administered and the second composition containing the extract of the plant belonging to the genus Ludwigia, each as the primary ingredient or component, to each of which may contain one kind of the secondary ingredient or component. The following is the cases where two kinds of the secondary ingredients or components are added to the primary ingredient or component.

Case No. 9

A diabetic patient, 168 cm in height and 76 kilograms in weight, was administered with the first composition prepared in Example No. 13 four times per day for two months.

The diabetic patient had subjective symptoms such as malaise, polyuria, thirst, polyphagia, and nervous disorders such as convulsion of the legs and numbness at the part of the great toes of the feet. Laboratory test results were as follows: urine glucose: (++); blood glucose levels under glucose load by applying 75 grams of glucose: 196 mg/dl before glucose load, 365 mg/dl in 60 minutes after glucose load, 271 mg/dl in 120 minutes after glucose load; and 202 mg/dl in 180 minutes after glucose load; GOT: 31 iu/l; GPT: 25 iu/l; γ-GTP: 58 mu/ml; LDH: 336 iu/l; and neutral fat: 237 mg/dl.

After the two-month administration of the first composition, the diabetic patient no longer had any subjective symptoms such as malaise, thirst and nervous disorders. Further, no abnormality was observed in urine. The laboratory test results indicate as follows: urine glucose: (−); blood glucose levels under glucose load by applying 75 grams of glucose: 91 mg/dl before glucose load, 162 mg/dl in 60 minutes after glucose load, 130 mg/dl in 120 minutes after glucose load and 98 mg/dl after glucose load; GOT: 28 iu/l; GPT: 23 iu/l; and γ-GTP: 57 mu/ml.

After the completion of administration of the first composition for two months, the diabetic patient was continuously administered with the second composition prepared in Example No. 14 for another one month.

After one month during which the second composition was administered, the diabetic patient was subjected to investigations for subjective symptoms and laboratory tests. The diabetic patient no longer felt any subjective symptoms. The laboratory test results were as follows: urine glucose: (−); and blood glucose levels under glucose load by applying 75 grams of glucose: 81 mg/dl before glucose load, 105 mg/dl in 60 minutes after glucose load, and 90 mg/dl in 120 minutes after glucose load. For this patient, it was found that the blood glucose before glucose load, i.e. at AC, was lowered to a remarkable extent.

Further, the diabetic patient was subjected to investigations for subjective symptoms and laboratory tests in one months after the completion of administration of the second composition. The diabetic patient lost the body weight to 68.5 kilograms and still had no subjective symptoms. The laboratory test results were as follows: urine glucose: (−); and blood glucose levels under glucose load by applying 75 grams of glucose: 73 mg/dl before glucose load, and 98 mg/dl in 120 minutes after glucose load. It was further found that the patient had maintained its conditions for a prolonged period of time after the termination of administration of the second composition.

Case No. 10

A diabetic patient was administered with the first composition as prepared in Example No. 13 as drink or tea for two months and thereafter the second composition as prepared in Example No. 14 as drink or tea in substantially the same manner as in Case No. 9.

The subjective symptoms and laboratory test results were substantially the same as those performed in Case No. 9.

EFFECTS OF THE INVENTION

The composition for treating or curing diabetes mellitus according to the present invention can alleviate or diminish a variety of symptoms caused by or associated with diabetes mellitus and prevailing among diabetic patients and thereafter cause urine glucose and blood glucose levels to be reduced or lowered naturally to normal values, thereby treating and curing diabetes mellitus, particularly when the first composition containing an extract produced from the plant belonging to the genus Tithonia is administered in the form of an extract or tea for a certain period of time, more preferably for approximately two months, and thereafter the second composition containing an extract produced from the plant belonging to the genus Ludwigia is administered in the form of an extract or tea for a certain period of time shorter than the period of time for which the first composition is administered, more preferably for approximately one month.

As described hereinabove, the composition for treating or curing diabetes mellitus according to the present invention can alleviate or diminish the various symptoms caused by or associated with diabetes mellitus or prevailing among diabetic patients, followed by naturally reducing or lowering blood glucose levels. Particularly, the various symptoms prevailing among and suffering diabetic patients, such as malaise, polyuria, polyphagia, pollakiurea or impotence can be cured by administration of the compositions of the present invention. Further, the diseases complicated with diabetes mellitus such as infectious diseases in the urinary tracts, retinopathy, cataract, disorders of the liver functions, nervous disorders (e.g. numbness of the lower legs or abnormal perception) or nephropathy, can also be cured by administration of the compositions according to the present invention.

Unlike conventional drugs which are intended to forcibly reduce or lower blood glucose levels, the composition according to the present invention can be said to be more effective than those conventional ones in terms of the capability of causing low blood glucose levels and a prevention of re-elevation of blood glucose levels over a prolonged period of time, e.g. for ten years. During this period, the diabetic patients can behave as he or she is healthy by eating and drinking as if a healthy person.

After such a prolonged period of time have passed by, there is the risk or possibility that the blood glucose level would arise again. Although the mechanism and action of the composition according to the present invention upon diabetes mellitus are not clarified yet, it can be considered that the administration of the composition acts directly upon cells of peripheral tissues such as cells of the liver or adipose tissues to thereby allow an insulin-like action to occur. Further, the fact that diabetic patients are not required to administer the composition according to the present invention continuously is considered that the composition would act upon substances controlling the glucose metabolism and consequently form an antibody in the bodies of the diabetic patients in accordance with the antigen-antibody reaction, which is capable of suppressing the action of the such substances.

Further, as the mechanism of pharmacological effects of the composition according to the present invention, it is considered that the ingredients or components contained in the extract of the plant suitable for use with the present invention would act upon substances capable of diminishing or lowering the absorption of insulin in blood of diabetic patients and particularly protein polysaccharides contained therein are likely to be joined to insulin, thereby allowing them to enter into cells through cell membranes and diminishing abnormality in the glucose metabolism, followed by leading to curing diabetes mellitus.

Furthermore, since the composition for treating or curing diabetes mellitus according to the present invention may contain extracts of different kinds of the plants and/or vitamins and/or chitin and/or chitosan as the secondary ingredient or component, the composition can achieve the effects of the secondary ingredient or component, in addition to the effects to be achieved by the primary ingredient or component, thereby alleviating or diminishing various symptoms caused by or associated with diabetes mellitus or prevailing among diabetic patients.

The further feature of the composition according to the present invention resides in the fact that the composition of this invention does not cause diabetic patients to lower or reduce their blood glucose level too low.

In addition, even if healthy persons or any persons other than diabetic patients would drink or take the composition of the present invention, it would not cause their blood glucose levels whatsoever to vary to any extent. This also may serve as confirming that the antibody to the substance suppressing the formation of insulin is to be produced in the manner as described hereinabove.

What is claimed is:

1. A composition for reducing the blood sugar in treating diabetes mellitus comprising an extract from a plant selected from the genus Ludwigia, wherein said extract is obtained by immersing said plant in a pharmacologically acceptable solvent.

2. The composition of claim 1, wherein said plant selected from the genus Ludwigia is selected from the group consisting of *Ludwigia octovalvis* Raven, *Ludwigia prostrata* Roxb., and *Ludwigia epilolbioides* Maxim.

3. The composition of claim 1, wherein said extract is prepared by immersing said plant in said solvent at a ratio from about 1% to about 50% plant weight to solvent volume.

4. The composition of claim 3, wherein said extract is further concentrated.

5. A method for the preparation of a composition for reducing the blood sugar in treating diabetes mellitus, comprising the steps of:

a) obtaining an extract by immersing a plant selected from the Ludwigia in a pharmacologically acceptable solvent; and b) concentrating said extract.

6. The method of claim 5, wherein said plant selected from the genus Ludwigia is selected from the group consisting of *Ludwigia octovalvis* Raven, *Ludwigia prostrata* Roxb., and *Ludwigia epilolbioides* Maxim.

7. A method for reducing the blood sugar in treating diabetes mellitus comprising administering a composition comprising an extract from a plant selected from the genus Tithonia or from the genus Ludwigia, wherein said extract is obtained by immersing said plant in a pharmacologically acceptable solvent.

8. A method for reducing the blood sugar in treating diabetes mellitus comprising the steps of:

a) administering a composition comprising an extract from a plant selected from the genus Tithonia, wherein said extract is obtained by immersing said plant in a pharmacologically acceptable solvent; and b) administering subsequently a composition comprising an extract from a plant selected from the genus Ludwigia, wherein said extract is obtained by immersing said plant in a pharmacologically acceptable solvent.

* * * * *